(12) United States Patent
Lurie et al.

(10) Patent No.: US 8,011,367 B2
(45) Date of Patent: Sep. 6, 2011

(54) CPR DEVICES AND METHODS UTILIZING A CONTINUOUS SUPPLY OF RESPIRATORY GASES

(75) Inventors: Keith Lurie, Minneapolis, MN (US); Greg Voss, Lakeville, MN (US)

(73) Assignee: Advanced Circulatory Systems, Inc., Roseville, MN (US)

( * ) Notice: Subject to any disclaimer, the term of this patent is extended or adjusted under 35 U.S.C. 154(b) by 1129 days.

(21) Appl. No.: 11/679,693

(22) Filed: Feb. 27, 2007

(65) Prior Publication Data

US 2007/0221222 A1 Sep. 27, 2007

Related U.S. Application Data

(63) Continuation-in-part of application No. 11/127,993, filed on May 11, 2005, now Pat. No. 7,275,542, which is a continuation of application No. 10/660,366, filed on Sep. 11, 2003, now Pat. No. 6,938,618.

(51) Int. Cl.
*A61M 11/00* (2006.01)
(52) U.S. Cl. .......... 128/205.24; 128/204.26; 128/207.14
(58) Field of Classification Search ............ 128/203.11, 128/204.26, 204.28, 205.13, 205.24, 207.14
See application file for complete search history.

(56) References Cited

U.S. PATENT DOCUMENTS

| | | |
|---|---|---|
| 2,774,346 A | 12/1956 | Halliburton |
| 3,077,884 A | 2/1963 | Batrow et al. |
| 3,191,596 A | 6/1965 | Bird et al. |
| 3,216,413 A | 11/1965 | Mota |
| 3,307,541 A | 3/1967 | Hewson |
| 3,459,216 A | 8/1969 | Bloom et al. |
| 3,515,163 A | 6/1970 | Freeman |
| 3,662,751 A | 5/1972 | Barkalow et al. |

(Continued)

FOREIGN PATENT DOCUMENTS

CA 668771 8/1963

(Continued)

OTHER PUBLICATIONS

WIPO, Patent Cooperation Treaty (RO/US), Written Opinion and International Search Authority, Mar. 11, 2005, 5 pages, Int'l. Patent Appl. No. PCT/US2004/027772 filed Aug. 25, 2004.

(Continued)

*Primary Examiner* — Steven Douglas
(74) *Attorney, Agent, or Firm* — Kilpatrick Townsend and Stockton LLP

(57) ABSTRACT

A method for increasing circulation and providing oxygen to a patient in cardiac arrest includes the step of coupling an interface to the patient's airway, the interface providing access to the patient's respiratory system. A valve system is operably attached to the interface. Oxygen is delivered through the interface a rate of between about 1.0 to about 10.0 L/min to provide a continuous supply of oxygen to the patient. While supplying the oxygen, a body structure of the patient is manipulated to increase the magnitude and duration of the patient's negative intrathoracic pressure. During the manipulation, the valve system prevents additional respiratory gases from entering the lungs until a negative intrathoracic pressure level in the range from about −1 cm H2O to about −15 cm H2O, the valve system assisting in increasing the magnitude and duration of negative intrathoracic pressure thereby enhancing the amount of blood flow in the heart and lungs and lowering intracranial pressure, therein further increasing blood flow to the brain.

27 Claims, 7 Drawing Sheets

U.S. PATENT DOCUMENTS

| | | | |
|---|---|---|---|
| 3,669,108 | A | 6/1972 | Sundblom et al. |
| 3,794,043 | A | 2/1974 | McGinnis |
| 3,815,606 | A | 6/1974 | Mazal |
| 3,834,383 | A | 9/1974 | Weigl et al. |
| 3,875,626 | A | 4/1975 | Tysk et al. |
| 3,933,171 | A | 1/1976 | Hay |
| 4,041,943 | A | 8/1977 | Miller |
| 4,077,404 | A | 3/1978 | Elam |
| 4,166,458 | A | 9/1979 | Harrigan |
| 4,226,233 | A | 10/1980 | Kritzer |
| 4,259,951 | A | 4/1981 | Chernack et al. |
| 4,298,023 | A | 11/1981 | McGinnis |
| 4,316,458 | A | 2/1982 | Hammerton-Fraser |
| 4,320,754 | A | 3/1982 | Watson et al. |
| 4,349,015 | A | 9/1982 | Alferness |
| 4,397,306 | A | 8/1983 | Weisfeldt et al. |
| 4,424,806 | A | 1/1984 | Newman et al. |
| 4,446,864 | A | 5/1984 | Watson et al. |
| 4,449,526 | A | 5/1984 | Elam |
| 4,481,938 | A | 11/1984 | Lindley |
| 4,533,137 | A | 8/1985 | Sonne |
| 4,601,465 | A | 7/1986 | Roy |
| 4,809,683 | A | 3/1989 | Hanson |
| 4,827,935 | A | 5/1989 | Geddes et al. |
| 4,881,527 | A | 11/1989 | Lerman |
| 4,898,166 | A | 2/1990 | Rose et al. |
| 4,898,167 | A | 2/1990 | Pierce et al. |
| 4,928,674 | A | 5/1990 | Halperin et al. |
| 5,014,698 | A | 5/1991 | Cohen |
| 5,016,627 | A | 5/1991 | Dahrendorf |
| 5,050,593 | A | 9/1991 | Poon |
| 5,056,505 | A | 10/1991 | Warwick et al. |
| 5,109,840 | A | 5/1992 | Daleiden |
| 5,163,424 | A | 11/1992 | Kohnke |
| 5,184,620 | A | 2/1993 | Cudahy et al. |
| 5,193,544 | A | 3/1993 | Jaffe |
| 5,217,006 | A | 6/1993 | McCulloch |
| 5,235,970 | A | 8/1993 | Augustine |
| 5,263,476 | A | 11/1993 | Henson |
| 5,295,481 | A | 3/1994 | Geeham |
| 5,301,667 | A | 4/1994 | McGrail et al. |
| 5,305,743 | A | 4/1994 | Brain |
| 5,316,907 | A | 5/1994 | Lurie |
| 5,355,879 | A | 10/1994 | Brain |
| 5,359,998 | A | 11/1994 | Lloyd |
| 5,377,671 | A | 1/1995 | Biondi et al. |
| 5,392,774 | A | 2/1995 | Sato |
| 5,398,714 | A | 3/1995 | Price |
| 5,423,772 | A | 6/1995 | Lurie |
| 5,437,272 | A * | 8/1995 | Fuhrman .................. 128/203.12 |
| 5,452,715 | A | 9/1995 | Boussignac |
| 5,454,779 | A | 10/1995 | Lurie et al. |
| 5,490,820 | A | 2/1996 | Schock et al. |
| 5,492,116 | A | 2/1996 | Scarberry et al. |
| 5,496,257 | A | 3/1996 | Kelly |
| 5,517,986 | A | 5/1996 | Starr et al. |
| 5,549,581 | A | 8/1996 | Lurie |
| 5,551,420 | A | 9/1996 | Lurie et al. |
| 5,588,422 | A | 12/1996 | Lurie |
| 5,618,665 | A | 4/1997 | Lurie |
| 5,628,305 | A | 5/1997 | Melker |
| 5,632,298 | A | 5/1997 | Artinian |
| 5,643,231 | A | 7/1997 | Lurie |
| 5,645,522 | A | 7/1997 | Lurie et al. |
| 5,657,751 | A | 8/1997 | Karr, Jr. |
| 5,692,498 | A | 12/1997 | Lurie et al. |
| 5,697,364 | A | 12/1997 | Chua et al. |
| 5,704,346 | A | 1/1998 | Inoue |
| 5,722,963 | A | 3/1998 | Lurie |
| 5,730,122 | A | 3/1998 | Lurie |
| 5,735,876 | A | 4/1998 | Kroll et al. |
| 5,738,637 | A | 4/1998 | Kelly et al. |
| 5,782,883 | A | 7/1998 | Kroll et al. |
| 5,814,086 | A | 9/1998 | Hirschberg et al. |
| 5,827,893 | A | 10/1998 | Lurie |
| 5,919,210 | A | 7/1999 | Lurie |
| 5,927,273 | A * | 7/1999 | Federowicz et al. ..... 128/200.24 |
| 5,937,853 | A | 8/1999 | Ström |
| 5,977,091 | A | 11/1999 | Neiman et al. |
| 5,984,909 | A | 11/1999 | Lurie |
| 6,001,085 | A | 12/1999 | Lurie |
| 6,029,667 | A | 2/2000 | Lurie |
| 6,062,219 | A | 5/2000 | Lurie et al. |
| 6,078,834 | A | 6/2000 | Lurie |
| 6,155,257 | A | 12/2000 | Lurie et al. |
| 6,174,295 | B1 | 1/2001 | Cantrell et al. |
| 6,224,562 | B1 | 5/2001 | Lurie et al. |
| 6,234,985 | B1 | 5/2001 | Lurie et al. |
| 6,277,107 | B1 | 8/2001 | Lurie |
| 6,312,399 | B1 | 11/2001 | Lurie et al. |
| 6,425,393 | B1 | 7/2002 | Lurie et al. |
| 6,459,933 | B1 | 10/2002 | Lurie et al. |
| 6,463,327 | B1 | 10/2002 | Lurie et al. |
| 6,486,206 | B1 | 11/2002 | Lurie |
| 6,526,973 | B1 | 3/2003 | Lurie et al. |
| 6,536,432 | B2 | 3/2003 | Truschel |
| 6,578,574 | B1 | 6/2003 | Kohnke |
| 6,587,726 | B2 | 7/2003 | Lurie et al. |
| 6,604,523 | B2 | 8/2003 | Lurie et al. |
| 6,656,166 | B2 | 12/2003 | Lurie |
| 6,776,156 | B2 | 8/2004 | Lurie et al. |
| 6,792,947 | B1 | 9/2004 | Bowden |
| 6,863,656 | B2 | 3/2005 | Lurie |
| 6,935,336 | B2 | 8/2005 | Lurie et al. |
| 6,938,618 | B2 | 9/2005 | Lurie et al. |
| 6,986,349 | B2 | 1/2006 | Lurie |
| 7,032,596 | B2 | 4/2006 | Thompson et al. |
| 7,044,128 | B2 | 5/2006 | Lurie |
| 7,082,945 | B2 | 8/2006 | Lurie |
| 7,174,891 | B2 | 2/2007 | Lurie et al. |
| 7,185,649 | B2 | 3/2007 | Lurie |
| 7,195,012 | B2 | 3/2007 | Lurie |
| 7,195,013 | B2 | 3/2007 | Lurie |
| 7,204,251 | B2 | 4/2007 | Lurie |
| 7,210,480 | B2 | 5/2007 | Lurie et al. |
| 7,226,427 | B2 * | 6/2007 | Steen ............................. 601/44 |
| 7,275,542 | B2 | 10/2007 | Lurie et al. |
| 7,311,668 | B2 | 12/2007 | Lurie et al. |
| 7,682,312 | B2 | 3/2010 | Lurie |
| 7,766,011 | B2 | 8/2010 | Lurie |
| 7,836,881 | B2 | 11/2010 | Lurie et al. |
| 7,899,526 | B2 | 3/2011 | Benditt et al. |
| 2001/0029339 | A1 | 10/2001 | Orr et al. |
| 2002/0029030 | A1 | 3/2002 | Lurie et al. |
| 2002/0069878 | A1 | 6/2002 | Lurie et al. |
| 2002/0104521 | A1 * | 8/2002 | Ogushi et al. ............. 128/207.14 |
| 2002/0170562 | A1 | 11/2002 | Lurie et al. |
| 2002/0188332 | A1 | 12/2002 | Lurie et al. |
| 2003/0000526 | A1 | 1/2003 | Gobel |
| 2003/0037784 | A1 | 2/2003 | Lurie |
| 2003/0062040 | A1 | 4/2003 | Lurie |
| 2003/0062041 | A1 | 4/2003 | Keith et al. |
| 2003/0192547 | A1 | 10/2003 | Lurie et al. |
| 2004/0016428 | A9 | 1/2004 | Lurie |
| 2004/0058305 | A1 | 3/2004 | Lurie et al. |
| 2004/0200473 | A1 | 10/2004 | Lurie |
| 2004/0200474 | A1 | 10/2004 | Lurie |
| 2004/0211415 | A1 | 10/2004 | Lurie |
| 2004/0211416 | A1 | 10/2004 | Lurie |
| 2004/0211417 | A1 | 10/2004 | Lurie |
| 2004/0231664 | A1 | 11/2004 | Lurie et al. |
| 2005/0016541 | A1 | 1/2005 | Lurie et al. |
| 2005/0126567 | A1 | 6/2005 | Lurie et al. |
| 2005/0165334 | A1 | 7/2005 | Lurie et al. |
| 2005/0199237 | A1 | 9/2005 | Lurie et al. |
| 2005/0217677 | A1 | 10/2005 | Lurie |
| 2005/0267381 | A1 | 12/2005 | Benditt |
| 2006/0089574 | A1 | 4/2006 | Paradis |
| 2007/0021683 | A1 | 1/2007 | Benditt et al. |
| 2007/0221222 | A1 | 9/2007 | Lurie |
| 2007/0277826 | A1 | 12/2007 | Lurie |
| 2008/0047555 | A1 | 2/2008 | Lurie et al. |
| 2008/0108905 | A1 | 5/2008 | Lurie |
| 2008/0255482 | A1 | 10/2008 | Lurie |
| 2008/0257344 | A1 | 10/2008 | Lurie et al. |
| 2009/0020128 | A1 | 1/2009 | Metzger et al. |

| | | | |
|---|---|---|---|
| 2009/0277447 | A1 | 11/2009 | Voss et al. |
| 2010/0179442 | A1 | 7/2010 | Lurie |
| 2010/0319691 | A1 | 12/2010 | Lurie et al. |

FOREIGN PATENT DOCUMENTS

| | | |
|---|---|---|
| CA | 2077608 A1 | 3/1993 |
| DE | 24 53 490 A1 | 5/1975 |
| EP | 0 029 352 A1 | 5/1981 |
| EP | 0 139 363 A1 | 5/1985 |
| EP | 0 245 142 A1 | 11/1987 |
| EP | 0 367 285 B1 | 5/1990 |
| EP | 0 411 714 A1 | 2/1991 |
| EP | 0 509 773 A1 | 10/1992 |
| GB | 1 465 127 | 2/1977 |
| GB | 2 139 099 A | 11/1984 |
| WO | WO90/05518 A1 | 5/1990 |
| WO | WO93/21982 A1 | 11/1993 |
| WO | WO94/26229 A1 | 11/1994 |
| WO | WO95/13108 A1 | 5/1995 |
| WO | WO95/28193 A1 | 10/1995 |
| WO | WO96/28215 A1 | 9/1996 |
| WO | WO99/63926 A1 | 12/1999 |
| WO | WO01/70332 A1 | 9/2001 |
| WO | WO02/092169 A1 | 11/2002 |

OTHER PUBLICATIONS

Ambu International A/S "Directions for use of Ambu® CardioPump™", 8 pages.

Christenson, J.M., "Abdominal Compressions During CPR: Hemodynamic Effects of Altering Timing and Force", The Journal of Emergency Medicine, vol. 10, pp. 257-266, 1992.

Cohen, Todd J. et al. "Active Compression-Decompression Resuscitation: a Novel Method of Cardiopulmonary Resuscitation", Department of Medicine and the Cardiovascular Research Institute, UC San Francisco, American Heart Journal 126(5):1145-1150, 1992.

Cohen, Todd J. et al., "Active Compression-Decompression: A New Method of Cardiopulmonary Resuscitation", JAMA 267(21):2916-2923 (Jun. 3, 1992).

Dupuis, Yvon G., *Ventilators- Theory and Clinical Application*, pp. 447-448, 481, 496; Jan. 1986, Mosby Company.

Geddes, L.A. et al., "Inspiration Produced by Bilateral Electromagnetic, Cervical Phrenic Nerve Stimulation in Man," IEEE Transactions on Biomedical Engineering 38(9): 1047-1048 (Oct. 1991).

Geddes, L.A. et al., "Optimum Stimulus Frequency for Contracting the Inspiratory Muscles with chest Surface Electrodes to Produce Artificial respiration," Annals of Biomedical Engineering 18:103-108 (1990).

Geddes, L.A., "Electrically Produced Artificial Ventilation," Medical Instrumentation 22(5): 263-271 (1988).

Geddes, L.A., "Electroventilation—A Missed Opportunity?", Biomedical Instrumentation & Technology, Jul./Aug. 1998, pp. 401-414.

Glenn, William W.L. et al., "Diaphragm Pacing by Electrical Stimulation of the Phrenic Nerve," Neurosurgery 17(6):974-984 (1985).

Glenn, William W.L., et al., "Twenty Years of Experience in Phrenic Nerve Stimulation to Pace the Diaphragm," Pace 9:780-784 (Nov./Dec. 1986, Part I).

Kotze, P.L. et al., "Diaphragm Pacing in the Treatment of Ventilatory Failure,"San. Deel 68:223-224 (Aug. 17, 1995).

Laghi, Franco et al., "Comparison of Magnetic and Electrical Phrenic Nerve Stimulation in assessment of Diaphragmantic Contractility," American Physiological society, pp. 1731-1742 (1996).

Lindner, Karl H. et al., "Effects of Active Compression-Decompression Resuscitation on Myocardial and Cerebral Blood Flow in Pigs" Department of Anesthesiology and Critical Care Medicine, University of Ulm, Germany, Circulation 88(3):1254-1263, (Oct. 7, 1993).

Lurie, Keith G. et al., "Regulated to Death: The Matter of Informed Consent for Human Experimentation in Emergency Resuscitation Research," Cardiac Arrhythmia Center at the University of Minnesota, PACE 118:1443-1447 (Jul. 1995).

Mushin W. W. et al., "Automatic Ventilation of the Lungs—The Lewis-Leigh Inflating Valve," Blackwell Scientific, Oxford, GB, p. 838.

PCT International Search Report and Written Opinion mailed Sep. 23, 2008, International Application No. PCT/US08/60367, 11 pages.

International Search Report and Written Opinion of PCT/US2008/055112 mailed on Aug. 15, 2008, 7 pages.

US 5,584,866, 12/1996, Kroll et al. (withdrawn)

* cited by examiner

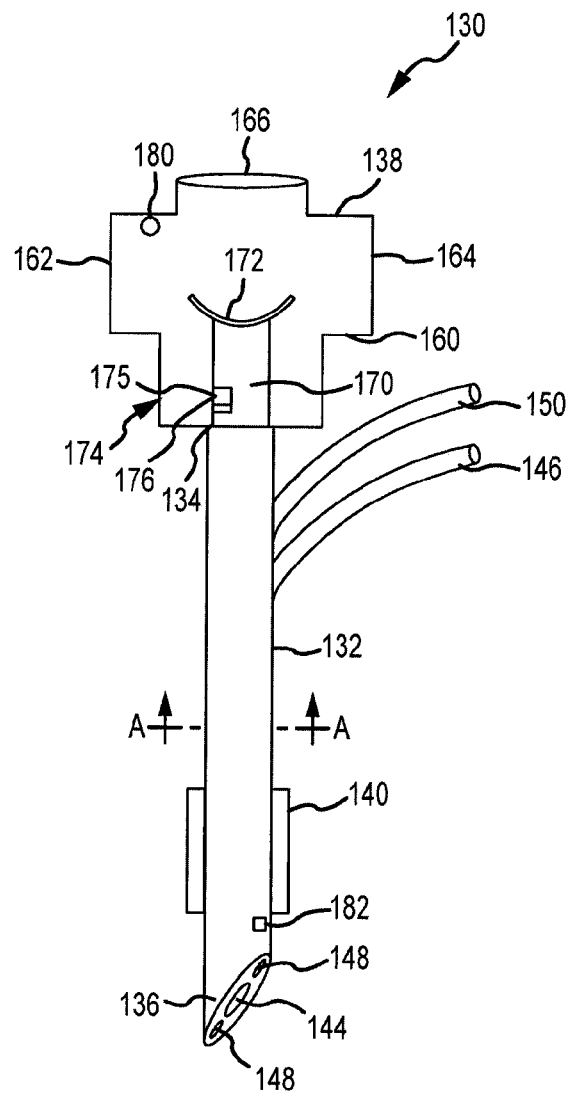
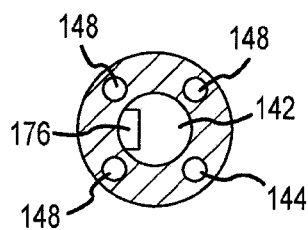
FIG. 8
FIG. 8A

CPR DEVICES AND METHODS UTILIZING A CONTINUOUS SUPPLY OF RESPIRATORY GASES

CROSS-REFERENCES TO RELATED APPLICATIONS

This application is a continuation in part application and claims the benefit of copending U.S. application Ser. No. 11/127,993, filed May 11, 2005, which is a continuation application of U.S. application Ser. No. 10/660,366, filed Sep. 11, 2003, now U.S. Pat. No. 6,938,618. The complete disclosures of all these references are herein incorporated by reference.

This application is related to U.S. application Ser. No. 10/660,462, filed Sep. 11, 2003, now U.S. Pat. No. 7,082,945, the complete disclosure of which is herein incorporated by reference.

BACKGROUND OF THE INVENTION

This invention relates generally to the field of blood flow, and in particular to the optimization of blood flow to the heart and brain in states of low blood pressure, elevated intracranial pressure, and cardiac arrest. In one aspect, the invention relates to the intentional manipulation of intrathoracic pressures to facilitate such blood flow. In another aspect, the invention relates to techniques for continuously supplying oxygen to the patient while techniques are employed to enhance the amount of negative intrathoracic pressure.

Inadequate blood flow can have serious consequences and may result from a variety of conditions. For example, those suffering from low blood pressure may have inadequate blood flow to the heart and brain. This is especially true when low blood pressure is the result of blood loss, such as from a serious wound, or in the setting of cardiac arrest.

Decreased cerebral perfusion secondary to increased intracranial pressure or cerebral artery occlusion is generally regarded as a leading cause of morbidity and mortality in the United States for children and young adults. Brain swelling and increased intracranial pressure from trauma and other illnesses often results in a decrease in blood flow to the brain with long-term neurological consequences. Because the skull cannot expand, the increased pressures within the brain can lead to death or serious brain injury. While a number of therapies have been evaluated in order to reduce brain swelling, including use of hyperventilation and steroids, an effective way to treat intracranial pressures remains an important medical challenge. As described in copending U.S. Pat. No. 7,082,945, the effects of high intracranial pressures may be addressed by decreasing intracranial pressure and increasing cerebral spinal fluid flow and, to a lesser extent, increasing blood flow to the brain. The complete disclosure of this application is herein incorporated by reference.

Similarly, those suffering from cardiac arrest lose essentially all blood flow. If not promptly restored, the loss of blood flow can lead to brain injury or death, among other ailments. A variety of techniques have been employed to treat patient's suffering from cardiac arrest. Such techniques typically require providing periodic ventilation. Such techniques can be challenging, especially when focusing on repeatedly compressing the chest.

BRIEF SUMMARY OF THE INVENTION

In one embodiment, the invention provides a method for increasing circulation and providing oxygen to a patient suffering from severely low blood pressure, such as a patient in cardiac arrest. According to the method, an interface is coupled to the patient's airway. The interface provides access to the patient's respiratory system. A valve system is operably attached with the interface. Oxygen is delivered through the interface at rate of between about 1.0 to about 10.0 L/min to provide a continuous supply of oxygen to the patient. While supplying the oxygen, a body structure of the patient (such as the chest) is manipulated to increase the magnitude and duration of the patient's negative intrathoracic pressure. During the manipulation, the valve system prevents additional respiratory gases from entering the lungs until a negative intrathoracic pressure level in the range from about −1 cm H2O to about −15 cm H2O is exceeded at which time the valve system permits additional respiratory gases to flow to the lungs. Periodically a positive pressure ventilation can be delivered to help provide for further respiratory gas exchange. In this way, the valve system assists in increasing the magnitude and duration of negative intrathoracic pressure thereby enhancing the amount of blood flow in the heart and lungs and lowering intracranial pressure, therein further increasing blood flow to the brain. By continuously supplying the oxygen, the patient is also ventilated while circulation is increased.

In one aspect, the interface comprises a ventilation tube comprising an inflow lumen and an outflow lumen. With such a configuration, gases exit the patient's lungs through the outflow lumen, and the oxygen is supplied through the inflow lumen.

The body structure may be manipulated by actively compressing the chest and then either passively or actively decompressing the chest. In some cases, the body structure may be manipulated using a pair of hands or a mechanical manually-operated or automated device to perform active compression/decompression CPR. This type of device may be secured to the patient's chest or by using a vest/carrass that actively expands the chest.

Periodically, a positive pressure breath may be provided to the patient to provide enhanced ventilation. Also, in some cases, at least one physiological parameter of the person, such as end tidal CO2, may be monitored. The positive pressure breath that is supplied may be based on the monitored parameter. Further, in some cases, carbon dioxide may be actively removed from the patient's lungs. In one aspect, the patient's lower limbs may be periodically squeezed. The timing of the squeezing of the lower limbs may be coordinated with the chest wall decompression or recoil phase of CPR.

In some cases, the patient may be suffering from cardiac arrest. However, such techniques may also be used when the patient is suffering from hypotension, including significant blood loss.

In one particular arrangement, the valve system includes a threshold inflow valve that is configured to open when the threshold negative intrathoracic pressure is exceeded. In one aspect, an oxygen source may be interfaced with the inflow lumen to continuously supply the oxygen to the patient's lungs. In another aspect, a balloon may be coupled to the ventilation tube, and the ventilation tube may include a balloon inflation lumen that may be inflated to secure the tube within the patient's airway. In other cases, oxygen could be continuous delivered through an alternative airway adjunct such as a laryngeal mask airway, a CombiTube, or a face mask firmly applied to the face.

The invention also provides an exemplary system for increasing circulation and providing oxygen to a patient. The system comprises an interface that is configured to interface with a patient's airway. A valve system is configured to be coupled to the interface, the valve system having an inflow valve that is configured to prevent respiratory gases from flowing to the lungs during the decompression or recoil phase of CPR until a negative intrathoracic pressure level in the range from about −1 cm H2O to −15 cm H2O is exceeded at which time the inflow valve opens. An oxygen source is configured to be coupled to the interface so as to continuously deliver oxygen through the inflow lumen at a rate of between about 1.0 to about 10.0 L/min. In this way, the valve system may be used to prevent respiratory gases from entering the lungs when manipulating a body structure while attempting to enhance the person's negative intrathoracic pressure. At the same time, the oxygen source provides ventilation to the patient. One advantage of the inflow valve is that it assists in increasing the magnitude and duration of negative intrathoracic pressure thereby enhancing the amount of blood flow in the heart and lungs and lowering intracranial pressure, therein further increasing blood flow to the brain.

In one aspect, the interface comprises a ventilation tube that is configured to be placed within the patient's airway. The ventilation tube has a proximal end, a distal end, an inflow lumen and an outflow lumen. The valve system is configured to be coupled to the outflow lumen, and the oxygen source is configured to be coupled to the inflow lumen.

In another aspect, a manipulation apparatus is employed to manipulate a body structure of the patient to increase the magnitude and duration of the patient's negative intrathoracic pressure. Also, the system may include at least one physiological sensor to measure at least one physiological parameter of the person. The physiological sensor may comprise an end tidal CO2 sensor.

A variety of manipulation apparatus may be used. For example, the manipulation apparatus may be an active compression/decompression device that is configured to be secured to the patient's chest, a vest/carrass that is configured to actively expand the chest or the like.

In one arrangement, a balloon is coupled to the ventilation tube near the distal end. Also, the ventilation tube may include a balloon inflation lumen. Further, the system may include a device to provide positive pressure ventilation to the patient through the valve system.

In a further embodiment, the invention provides a method for enhancing venous return to the heart. Such a method may be particularly useful for those suffering from cardiac arrest or low blood pressure where venous return to the heart is critical so that the returned blood may be re-oxygenated and circulated back through the body. The method may also be useful for those suffering from elevated intracranial pressure. In such cases, the decreased intrathoracic pressures cause a reduction in intracranial pressure, an increase in cerebral spinal fluid flow, and an increase in blood flow to the brain. Together, this results in decreased brain pressures and secondary brain injury. According to the method, a positive pressure breath can also be delivered to a person periodically. Respiratory gases are extracted from the person's airway following the positive pressure breath to create an intrathoracic vacuum to enhance venous return to the heart. The steps of delivering positive pressure breaths and extracting respiratory gases may be repeated to continue the treatment. In some embodiments, the timing of the positive pressure ventilation and generation of an vacuum to actively remove respiratory gases from the thorax and thereby decrease intracranial pressures and enhance venous return to the heart may be timed with the contraction and/or relaxation of the heart.

In some cases, such as when the person is breathing or during CPR, an impedance threshold valve may also be coupled to the person's airway. The threshold valve prevents airflow to the person's lungs when attempting to inspire until the threshold valve opens, thereby augmenting blood flow back to the heart. The threshold valve may be configured to open when the negative intrathoracic pressure exceeds about −6 cmH2O.

In another aspect, a flow limiting valve may be interfaced to the patient's airway to regulate the pressure and/or flow rate of the positive pressure breath. In a further aspect, a pressure source and a vacuum source may be interfaced to the person's airway to deliver the positive pressure breath and to extract the respiratory gases. Conveniently, the pressure source and the vacuum source may comprise a compressible bag system. In one aspect, the compressible bag system may be reconfigured to operate only as a pressure source. For example, the bag system may have a switch that is operated to place the bag system in a ventilate-only mode.

Another feature of the method is that the extracted respiratory gases may be exhausted to the atmosphere. In this way, the extracted air is not re-circulated to the person. In one aspect, the duration or amplitude of the positive pressure breaths or the extraction of the respiratory gases may be varied over time. If needed, the person may also be supplied with supplemental oxygen. Also, at least one physiological parameter of the person may be monitored, and the positive pressure breath or the extraction of respiratory gases may be varied based on the monitored parameter. Examples of physiological parameters include end tidal CO2, oxygen saturation, blood pressure, airway pressure, cardiac output and the like. Information on the measured parameter may be transmitted to a remote receiver In one particular aspect, the respiratory gases may be extracted upon recoiling of the compressible bag system. The volume of the positive pressure breath may also be measured.

In a further aspect, the intrathoracic vacuum lowers the person's intrathoracic pressure to about −1 mm Hg to about −20 mm Hg. This may be done using an intrathoracic vacuum in the range from about −2 mm Hg to about −60 mm Hg.

The invention also provides a method for treating a person suffering from cardiac arrest. According to the method, a person's chest is repeatedly compressed. Respiratory gases are prevented or impeded from flowing to the person's lungs for at least some time between chest compressions. Periodically, a positive pressure breath is delivered to the person. Respiratory gases are extracted from the person's airway following the positive pressure breath to create an intrathoracic vacuum to enhance venous return to the heart. If needed, an impedance threshold valve may be coupled to the person's airway to prevent or impede the flow of respiratory gases.

The invention also provides a device for manipulating intrathoracic pressures. The device comprises a compressible bag structure, and an interface member that is coupled to the bag structure for interfacing with a person's airway. A one way forward valve is coupled to the bag structure to permit respiratory gases to flow to the person's airway upon compression of the bag structure. Also, a one way exit valve is coupled to the bag structure to permit respiratory gases to be pulled from the person's airway upon decompression of the bag structure, thereby producing a negative intrathoracic pressure.

The forward valve and the exit valve may take a variety of forms, such as a spring loaded check valve, a fish mouth valve, a ball valve, a disc valve, a baffle, a magnetic valve, an electronic valve, and the like. In one aspect, the bag structure is configured to produce a vacuum in the range from about −2 mm Hg to about −60 mm Hg to produce a negative intrathoracic pressure in the range from about −1 mm Hg to about −20 mm Hg.

Optionally, an impedance threshold valve may be coupled to the compressible bag structure. The threshold valve is configured to permit respiratory gases to flow to the person's lungs once a certain negative intrathoracic pressure is exceeded. In another aspect, a flow limiting valve may be coupled to the compressible bag to regulate the flow of respiratory gases to the patient's lungs upon compression of the bag structure. Optionally, a switch may be provided for permanently closing the exit valve.

In a further aspect, an exhaust valve may be coupled to the bag structure to permit respiratory gases pulled from the person's airway to be exhausted to the atmosphere. Also, an oxygen source may be used to provide supplemental oxygen to the person through the interface member. Further, at least one physiological sensor may be operably coupled to the compressible bag structure to measure at least one physiological parameter of the person. A transmitter may be coupled to the sensor to transmit information on the measured parameter to a remote receiver.

In one aspect, a regulation valve may be coupled to the bag structure to regulate the rate of flow of respiratory gases to the person's airway and/or the pressure of the respiratory gases delivered to the person's airway. In a further aspect, the bag structure may comprise a ventilation chamber that supplies respiratory gases through the forward valve upon compression of the bag structure and an expiration chamber that receives respiratory gases from the person through the exit valve upon decompression of the bag structure. Also, the bag structure may further comprise a venturi system that pulls respiratory gases from the person's lungs upon decompression of the bag structure. The bag structure may also constructed of an elastomeric or other spring-like material to permit it to decompress.

BRIEF DESCRIPTION OF THE DRAWINGS

FIG. 8 illustrates the system of FIG. 7 when the threshold valve opens to permit respiratory gases to flow to the patient's lungs.

FIG. 8A is a cross-sectional view of the ventilation tube of FIG. 8 taken along lines A-A when the threshold valve is open.

DETAILED DESCRIPTION OF THE INVENTION

Figure 1:
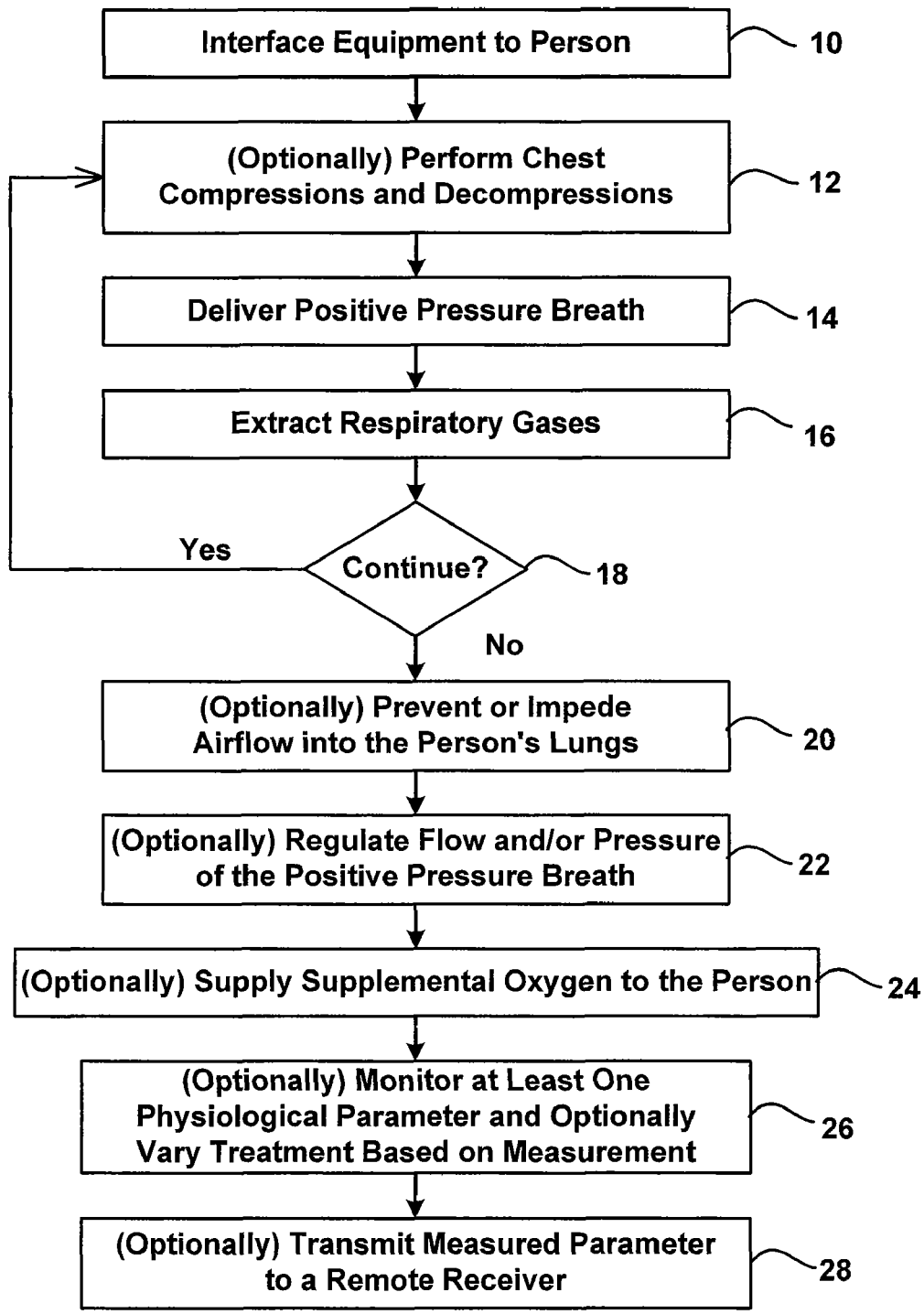
FIG. 1 is a flow chart illustrating one method for enhancing venous return to the heart according to the invention.

The invention may be useful in optimizing blood flow to the heart and brain in states of low blood pressure, head trauma, cardiac arrest and the like. For those suffering from head trauma, venous return to the chest may reduce intracranial pressures as described in U.S. Pat. No. 7,082,945, the complete disclosure of which is herein incorporated by reference. In some cases, the invention also provides techniques for providing adequate oxygenation in a patient who is receiving any one of a variety of closed-chest CPR techniques. Such techniques may include standard CPR, CPR with a compression band, CPR with a compression wrench, active compression decompression (ACD) CPR, and the like For those with low blood pressure, the increased circulation may help to increase their blood pressure. For those in cardiac arrest, blood circulation created by the invention serves to help maintain vital organ functions until successful resuscitation.

In order to provide such circulation, in one aspect the invention may utilize any device capable of delivering a positive pressure breath followed by the creation of a vacuum to lower the person's intrathoracic pressure. This may be performed with a mechanical ventilator, a ventilation bag and the like. In other cases, ventilation may be provided by continuously supplying a low level of oxygen to the patient while manipulating a body structure in an attempt to create a greater amount of negative intrathoracic pressure. In some cases, a CPAP machine may be used to supply the oxygen.

One embodiment utilizes a ventilator bag that may be compressed and then released to deliver and then extract air from the person. Such a bag may include a valve system that permits a positive pressure breath to be delivered when compressing the bag (referred to as the inspiratory phase) and then immediately pull a vacuum as the bag is released to cause the pressure within the chest to fall less than atmospheric pressure during the expiratory phase.

In some cases, the bag may include a threshold valve as described in U.S. Pat. Nos. 5,551,420; 5,692,498; 6,062,219; 5,730,122; 6,155,257; 6,234,916 and 6,224,562; 6,986,349 and Ser. No. 10/40149, filed Mar. 28, 2003 ("Diabetes Treatment Systems and Methods", 09/966,945, filed Sep. 28, 2001 and 09/967,029, filed Sep. 28, 2001, the complete disclosures of which are herein incorporated by reference. This valve arrangement may be used to prevent air from entering the person if the pressure within the chest is mechanically manipulated to fall (such as during the decompression phase of manual CPR or ACD CPR) during the expiratory phase.

In some cases, the rescuer may switch the operation from a "push-pull" ventilator to one that delivers only positive pressure ventilation, such as is traditional with most ventilator bags (e.g., an AMBU bag).

One reason for pulling the vacuum during the expiratory phase is to lower the intrathoracic pressure within the chest after each positive pressure ventilation. This negative pressure is transferred to the right heart and lungs, drawing more venous blood back from the extra-thoracic vasculature, and may be used to treat low blood pressure, head trauma and cardiac arrest.

The device may be configured to be hand-held, light weight and portable. As the bag decompresses, it "recharges" itself so that more air is available during the next squeeze. Optionally, a foot peddle may be connected to help develop a greater or more sustained vacuum. It may also include a timing device to provide feedback to the rescuers on how often to ventilate the patient. It may further include a regulator to limit the amount of pressure that builds up with each positive pressure ventilation to prevent stomach insufflation. One example of such a regulator is the SMART BAG®, commercially available from Mediline.

Referring now to FIG. 1, one method for enhancing blood circulation will be described. In so doing, it will be appreciated that such techniques may be used to treat those suffering from head trauma, low blood pressure, and cardiac arrest, among others.

At step 10, the process may begin by interfacing the appropriate equipment to the person. This may include, for example, a pressure and a vacuum source (such as a bag-valve system having a face mask), an impedance threshold valve, a positive pressure flow regulator, one or more physiological sensors, a transmitter for transmitting measured signals to a remote receiver, a metronome or other timing device to tell the rescuer when to ventilate and/or create a vacuum, an oxygen source and the like.

If the person is in cardiac arrest, the rescuer may perform CPR by performing chest compressions and decompressions as is known in the art. This is illustrated in step 12.

At step 14, a positive pressure breath is delivered to the person. This is immediately followed by the extraction of respiratory gases to lower the person's intrathoracic pressure as shown in step 16. Steps 12-16 may be repeated as necessary as shown in step 18. If the person is in cardiac arrest, the steps of delivering a breath and extracting respiratory gases are performed about once for every 5 to 20 chest compressions. The positive pressure breath may be delivered for about 0.5 to about 2.0 seconds while the vacuum may be produced for about 1 to about 10 seconds. The volume of air delivered may be in the range from about 4 ml/kg to about 20 ml/kg. The negative intrathoracic pressure created may be in the range from about −1 mmHg to about −20 mmHg. To create the pressure the generated vacuum may be about one to about three times this amount.

For those suffering from low blood pressure or elevated intracranial pressure, steps 14 and 16 may be continuously performed as long as treatment is needed. The positive pressure breath may last about 0.5 to about 3 seconds and have a volume of about 4 ml/kg to about 20 ml/kg. The vacuum may be produced immediately after the positive pressure breath and last about 1 second to a bout 6 seconds. The resulting negative intrathoracic pressure may be about −1 mm Hg to about −20 mm Hg and may be producing using a vacuum that is one to about three times this amount. Particular techniques for supplying the breath and extracting gases are described hereinafter with respect to FIGS. 5A-5C. Also, it will be appreciated that the vacuum may be producing using a flow of gases or with no flow, and the time and/or amount of the vacuum may be varied.

As shown in step 20, an impedance threshold valve or other device may be used to prevent or impede respiratory gases from entering the patient's lungs. This may be done, for example, when performing CPR. During decompression after the chest, air is typically drawn into the person's airway. Using an impedance valve, air is prevented from rushing in until a certain negative intrathoracic pressure is reached. At this time, the valve opens to permit gases to flow to the lungs. Such techniques are described in the references incorporated herein. For CPR applications, the valve may be set to open when the negative intrathoracic pressure exceeds about −4 $cmH_2O$ to about −15 $cmH_2O$. Such an impedance valve may also be used in non-CPR applications as well when the person inspires. In such cases, the valve may be set to open at about −3 cm $H_2O$ to about −12 $cmH_2O$.

In step 22, the volume, rate and or pressure of the positive pressure breath may be regulated. In this way, the patient may be protected against insufflation. In step 24, supplemental oxygen may be supplied to the patient. This may be supplied based on measured parameter as described below. Also, the oxygen may be delivered to the bag-valve system.

In step 26, one or more physiological parameters may optionally be monitored. The treatments described herein may be varied based on the measured parameters. Examples of such parameters include end tidal $CO_2$, oxygen saturation, blood pressure, cardiac output and the like. Other parameters as well as equipment and sensors that maybe be used are described in copending U.S. application Ser. No. 10/660,462, filed on the same date as the present application (and incorporated therein by reference) as well as in the other references incorporated herein. These may be coupled to a controller or other computer to record the measurements, display the measured parameters, recommend or control a specific treatment and the like.

As shown in step 28, information on the measured parameter may also be transmitted to a remote receiver. This may be over a variety of communication paths or networks, such as wireless networks, cell phones, local area networks, the Internet and the like. This information may be used to evaluate the treatment, monitor the quality of treatment, and command a treatment or the like. For example, the information may be transmitted to a hospital or health care facility where a physician may recommend how to apply the positive pressure breaths or extract the respiratory gases.

Figure 2:
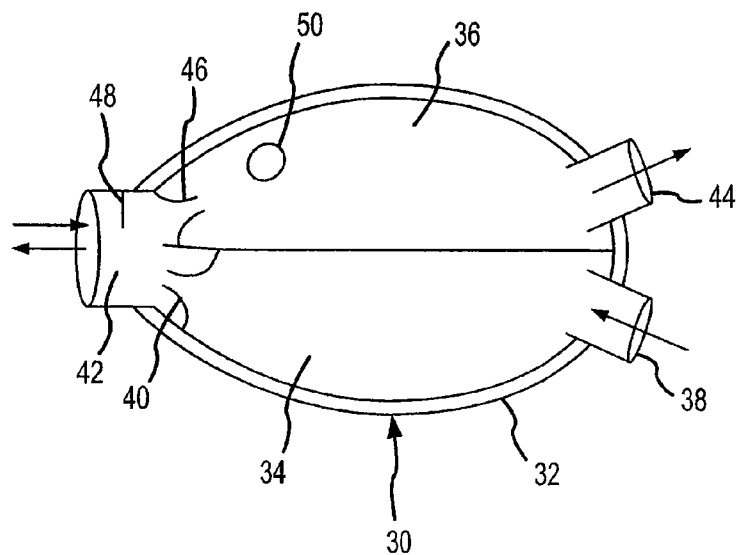
FIG. 2 is a schematic diagram of one embodiment of a bag-valve resuscitation system according to the invention.

Referring now to FIG. 2, one embodiment of a bag-valve resuscitator 30 will be described. Resuscitator 30 may be used in association with any of the methods described herein. Resuscitator 30 comprises a compressible bag 32 that is divided into a supply chamber 34 and an exit chamber 36. Bag 32 may be constructed of an elastomeric material that permits bag 32 to self-expand after it has been compressed. Optionally, an elastomeric material may be placed in one or both of the chambers to facilitate expansion of bag 32 after it has been compressed. Bag 32 also includes an entrance port 38 and a one-way inflow valve 40. When bag 32 is compressed, air, oxygen or other respiratory gases in supply chamber 34 are forced through inflow valve 40 and into a conduit 42 where they may be supplied to a person's airway. Optionally, an interface may be coupled to conduit 42 to couple resuscitator 30 to the patient. Such interfaces may include facial masks, endotracheal tubes, and the like. When bag 32 is released, it expands to its normal position. In so doing, inflow valve 40 closes allowing air or other respiratory gases to flow into chamber 34. Optionally, a flow restrictive device may be used to regulate the flow of air into conduit 42. This may provide a fixed resistance or a variable resistance.

Bag 32 also includes an exit port 44 and a one way outflow valve 46. When bag 32 is compressed, valve 46 closes and gases in chamber 36 may exit through port 44. As bag 32 expands, valve 46 opens to pull respiratory gases from the patient's airway. Hence, a positive pressure breath may be delivered when bag 32 is compressed and gases may be extracted when bag 32 is released. In so doing, the person's intrathoracic pressure is lowered to pull venous blood back into the chest.

Optionally, one or more sensors 48 may be incorporated into or coupled to resuscitator 30. Examples of sensors that may be used include any of those described or incorporated herein. As another option, a timer 50 may be coupled to or associated with bag 32. Timer 50 may be a flashing light, a speaker or the like to indicate when bag 32 should be compressed. This information may be pre-programmed or varied based upon measurements from sensor 48.

Figure 3:
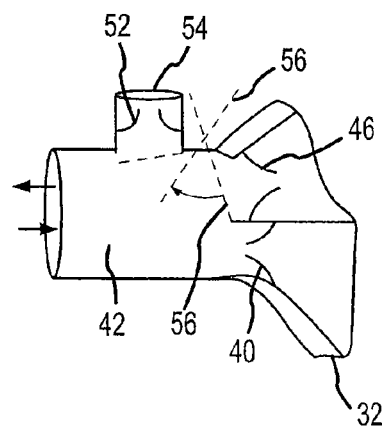
FIG. 3 illustrates a valve arrangement of the system of FIG. 2 along with a positive end expiratory pressure valve according to the invention.

As shown in FIG. 3, conduit 42 may be modified to include a positive end expiratory pressure (PEEP) valve 52 for non-breathing patients. This is located in a non-breather port 54.

PEEP valve 52 may be used when the resuscitator bag is switched from one device capable of "pushing and pulling" to one that is locked in the "traditional" positive pressure ventilator mode only. However, in some cases, PEEP valve 52 may be used intermittently, such as every other or every third ventilation cycle.

Resuscitator 30 may also include a switch or a closure valve 56 that may move to a position that blocks outflow valve 46. In so doing, the "pull" feature is turned off so that respiratory gases are not actively extracted during the expiratory phase. In another position, valve 56 may be moved to a position closing non-breather port 54. This option allows for standard positive pressure ventilation and for push/pull ventilation.

As another option, an impedance threshold valve may be positioned over conduit 42 or anywhere between the bag and the patient. This valve is particularly useful when performing CPR. When bag 32 is compressed, gases flow through the threshold valve and to the patient to provide proper ventilation. When performing CPR respiratory gases exiting the patient during compression of the chest pass through the impedance valve and out valve 46. During decompression of the chest, gases are prevented from entering the patient's lungs because of the impedance valve. This valve opens when a certain negative intrathoracic pressure is achieved when opened gases may enter conduit 42 through valve 40. Such an impedance valve is described in the references incorporated herein.

Figure 4:
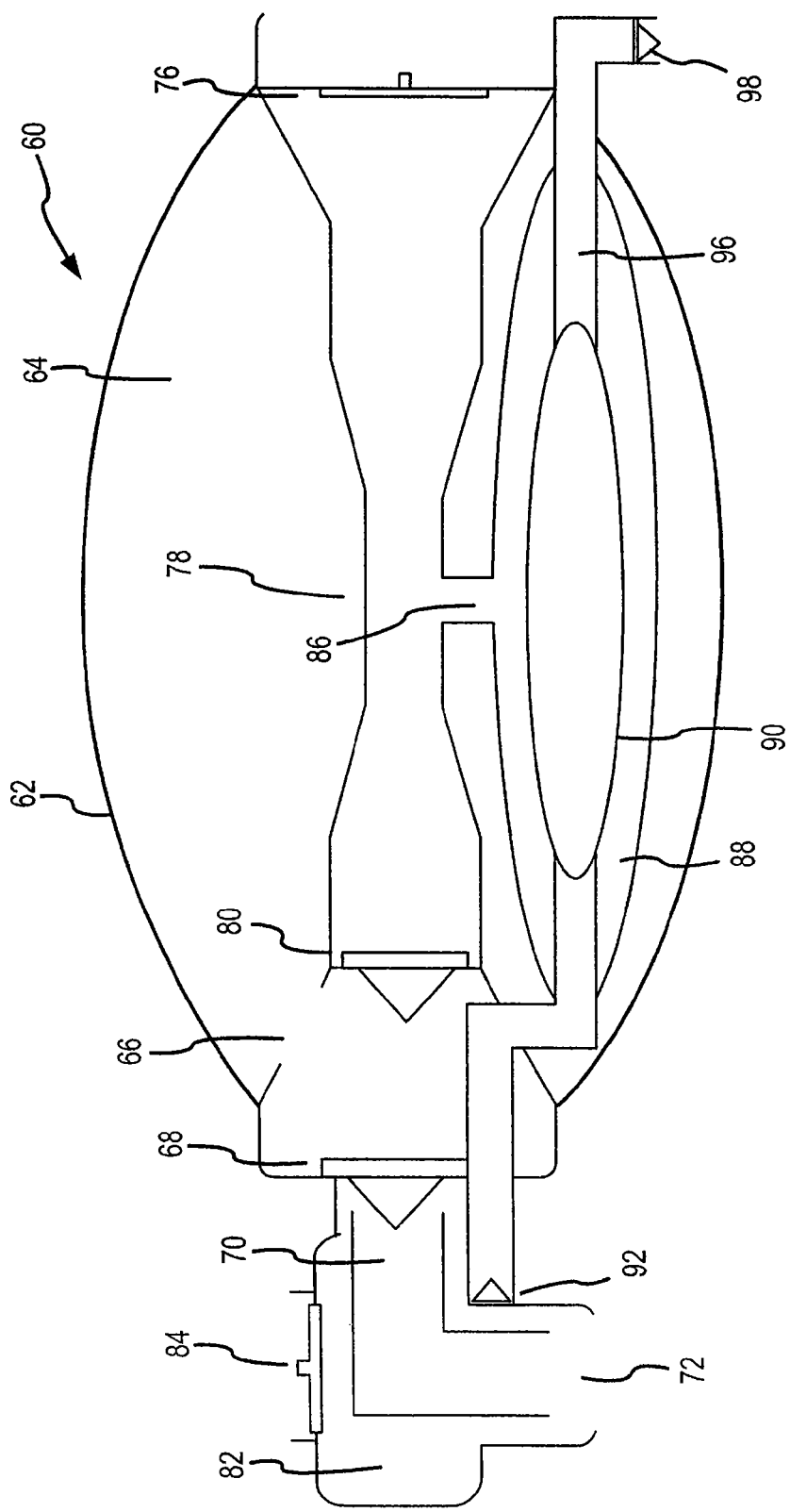
FIG. 4 is a schematic diagram of another embodiment of a bag-valve resuscitation system according to the invention.

FIG. 4 illustrates another embodiment of a bag-valve resuscitator 60 that comprises a compressible bag 62 that is constructed of an elastomeric material so that it will expand to its original shape following a compression. Bag 62 includes a main ventilation chamber 64 that is filled with air or other respiratory gases. When bag 62 is compressed, air in chamber 64 is directed through a ventilation port 66, through a fish mouth valve 68 and into a ventilation tube 70 where it is supplied to the patient through a patient support 72.

Ventilation chamber 64 is refilled as bag 62 is released and returns to its uncompressed shape. More specifically, as bag 62 decompresses, a negative pressure within main ventilation chamber 64 is produced. This opens a one way valve 76 allowing air to flow through a venturi tube 78, through a fish mouth valve 80, through ventilation port 66 and into chamber 64.

Following ventilation, passive expiratory gases from the patient may flow through patient port 72, into an expiratory chamber 82 and out a one way valve 84.

The generation of the negative intrathoracic pressure occurs during the passive recoil or decompression of bag 62. More specifically, air flowing through venturi tube 78 creates a venturi effect in tube 86. This creates a negative pressure within a negative chamber 88. In turn, this cases a secondary chamber 90 (which is collapsed) to pen, thereby including air flow through a fish mouth valve 92, through a supply tube 94 and into secondary chamber 90. Secondary chamber 90 may hold a volume of about 100 milliliters to about 150 milliliters when filled.

When bag 62 is again compressed, gas stored in secondary chamber 90 is directed through an exhaust tube 96 and expelled through a fish mouth valve 98.

Hence, resuscitator 60 may be used in any of the procedures described herein. Also, resuscitator 60 may include any of the other features described in connection with other embodiment described herein, such as flow regulators, threshold valve, sensors, PEEP valves, switches and the like.

Figure 5A:
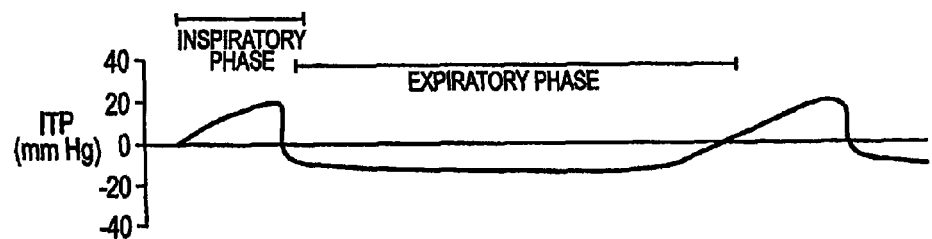
FIGS. 5A-5C show three graphics illustrating patterns for delivering a positive pressure breath and extracting respiratory gases according to the invention.
Figure 5B:
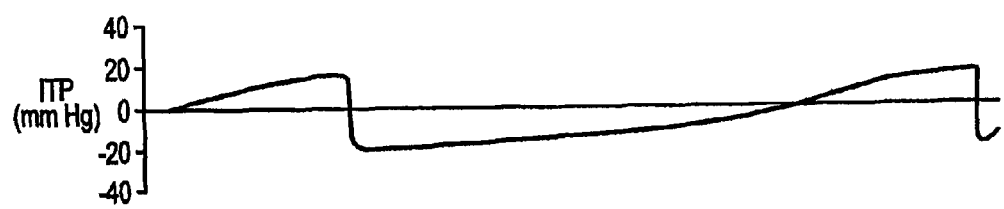
Figure 5C:

The manner in which positive pressure breaths and the vacuum are created may vary depending upon a particular application. These may be applied in a variety of waveforms having different durations and slopes. Examples include using a square wave, biphasic (where a vacuum is created followed by positive pressure, decay (where a vacuum is created and then permitted to decay), and the like. Three specific examples of how this may occur are illustrated in FIGS. 5A-5C, although others are possible. For convenience of discussion, the time during which the positive pressure breath occurs may be defined in terms of the inspiratory phase, and the time during which the intrathoracic pressure is lowered may be defined in terms of the expiratory phase. As shown in FIG. 5A, respiratory gases are quickly supplied up to a pressure of about 22 mmHg. This is immediately reversed to a negative pressure of about −10 mmHg. This pressure is kept relatively constant until the end of the expiratory phase where the cycle is repeated. In some cases, the cycle may go from a push-pull every breath to a push, then push-pull every other breath or every third breath, i.e. as a 2:1 or 3:1 push:pull option.

In FIG. 5B, the positive pressure is more slowly applied. When reaching a pressure of about 10 to about 15 mmHg, the pressure is rapidly reversed to a negative pressure of about −20 mmHg. The negative pressure gradually declines to about 0 mmHg at the end of the expiratory phase. The cycle is then repeated. Hence, in the cycle of FIG. 5B, the positive pressure is reduced compared to the cycle in FIG. 5A, and the negative pressure is initially lower, but allowed to gradually increase. The technique is designed to help reduce a possible airway collapse.

In FIG. 5C, the positive pressure is brought up to about 20 mmHg and then immediately brought down to about 0 mmHg. The negative pressure is then gradually increased to about −20 mmHg toward the end of the expiratory phase. This cycle is designed to help reduce a possible airway collapse.

In other embodiments, the invention provides techniques for providing adequate oxygenation while simultaneously increasing circulation. To increase circulation, one or more body parts may be manipulated. Some techniques for increasing circulation include performing traditional CPR, performing vest CPR, performing active compression/decompression (ACD) CPR, using an iron lung, a band to automatically compress and the chest, a sternal piston such as the Michigan Instrument's Thumper Device, and the like.

While performing any of these techniques, respiratory gases may be prevented or partially hindered from reaching the lungs when the chest recoils or is actively lifted or expanded. The gases may be restricted from flowing to the lungs using any of the valve systems described herein, including those incorporated by reference. Such valve systems may have a threshold valve that prevents respiratory gases from entering the lungs until a threshold pressure in the range from about −1 cm $H_2O$ to about −20 cm $H_2O$ is exceeded. At this point, the valve opens and respiratory gases are permitted to reach the lungs. By restricting gas flow to the lungs, the negative intrathoracic pressure is enhanced, both in terms of magnitude and duration.

To provide adequate oxygenation, a constant supply of oxygen may be supplied to the patient's lungs. This supply of oxygen is independent of the inflow of gases permitted by the threshold valve. The amount of oxygen supplied is critical in that if too much is supplied, a sufficient amount of negative intrathoracic pressure may not be created. If too little, the patient may not be adequately oxygenated. Hence, oxygen may be supplied at a rate in the range from about 1 L/min to about 10 L/min. In this way, the need to periodically deliver a positive pressure breath may be eliminated. However, such positive pressure breaths may be provided if desired. Also, in some cases, measures may be taken to remove carbon dioxide from the lungs.

The techniques to increase circulation may be used when the patient is in cardiac arrest. However, such techniques may also be used when the patient is hypotensive. Other disease states include severe hypotension secondary to blood loss, sepsis, cerebral vascular accident, and heart failure.

Figure 6:
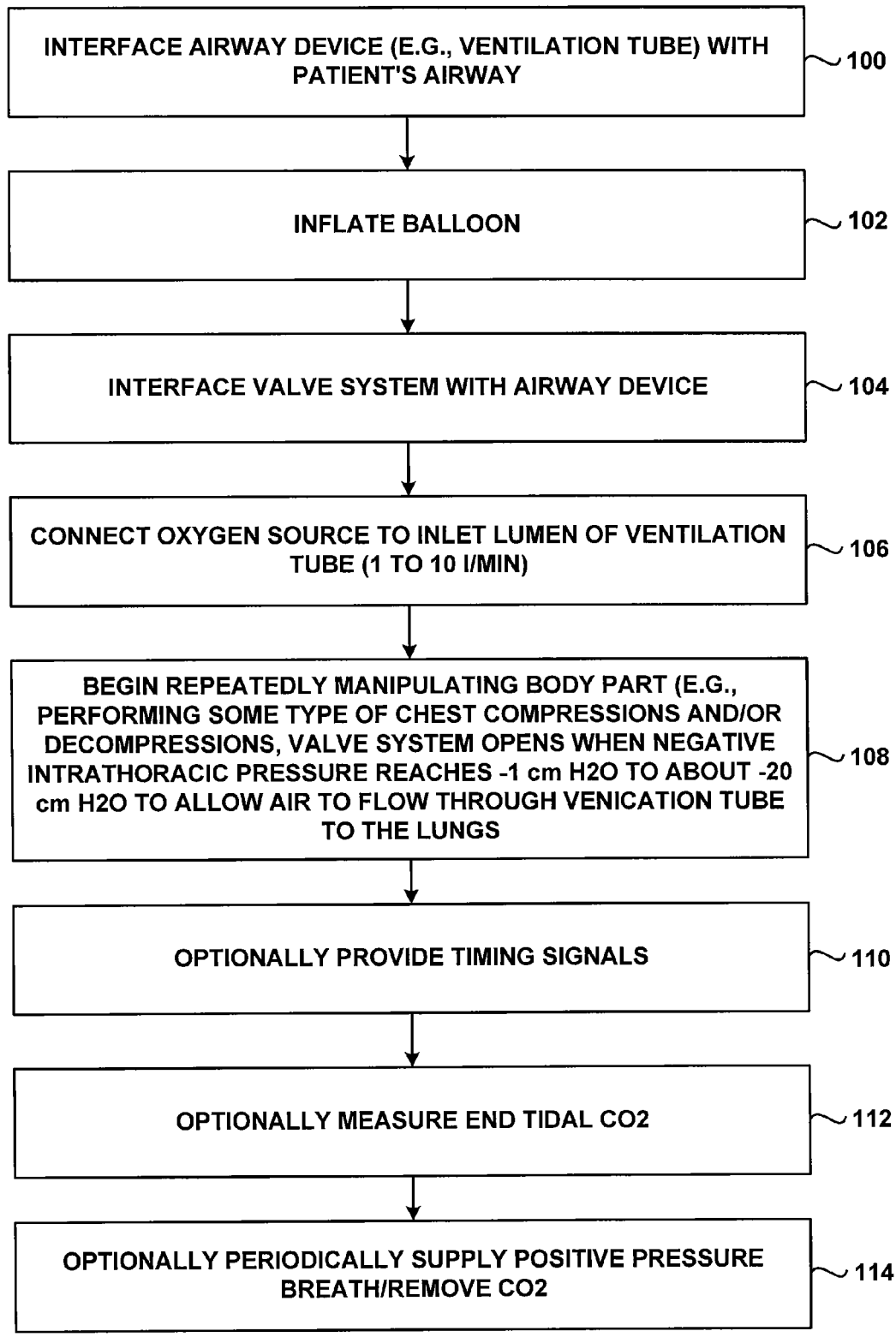
FIG. 6 illustrates a flow chart showing one method for increasing circulation and providing oxygenation to a patient according to the invention.

Referring now to FIG. 6, one method for increasing circulation while providing ventilation will be described. As shown in step 100, an airway device is interfaced with the patient. A variety of airway devices may be used, such a ventilation tube, a laryngeal airway, a facial mask, CombiTube, Obturator Airway, the King LTD mask, or the like. A balloon on the ventilation tube may be inflated to seal the tube in the person's trachea as shown in step 102. Either before or after the airway device is interfaced with the patient, a valve system is coupled with the airway device as shown in step 104. An oxygen source is also coupled to an inlet lumen of the ventilation tube as shown in step 106. The oxygen source provides a continuous supply of oxygen to the patient's lungs. The oxygen may be supplied at a rate in the range from about 1 L/min to about 10 L/min.

While supplying the oxygen, a body part is repeatedly manipulated to repeatedly enhance the patient's negative intrathoracic pressure. For example, the patient's chest may be compressed and then lifted as shown in step 108. When the patient's negative intrathoracic pressure exceeds a certain amount, the valve system operates to permit respiratory gases to flow to the lungs. On some cases, the negative intrathoracic pressure may reach about −1 cm H2O to about −20 cm H2O before the valve system permits the gases to flow to the lungs.

A variety of optional steps may be included as part of the method. For example, as shown in step 110, timing signals may be provided to assist a rescuer in performing chest compressions and/or decompressions. In step 112, the amount of $CO_2$ in a patient may be monitored, such as by sensing end tidal $CO_2$. If too great, measures may be taken to remove the $CO_2$. For example, in step 114, a positive pressure breath may be provided, followed by a vacuum to remove the $CO_2$.

Figure 7:
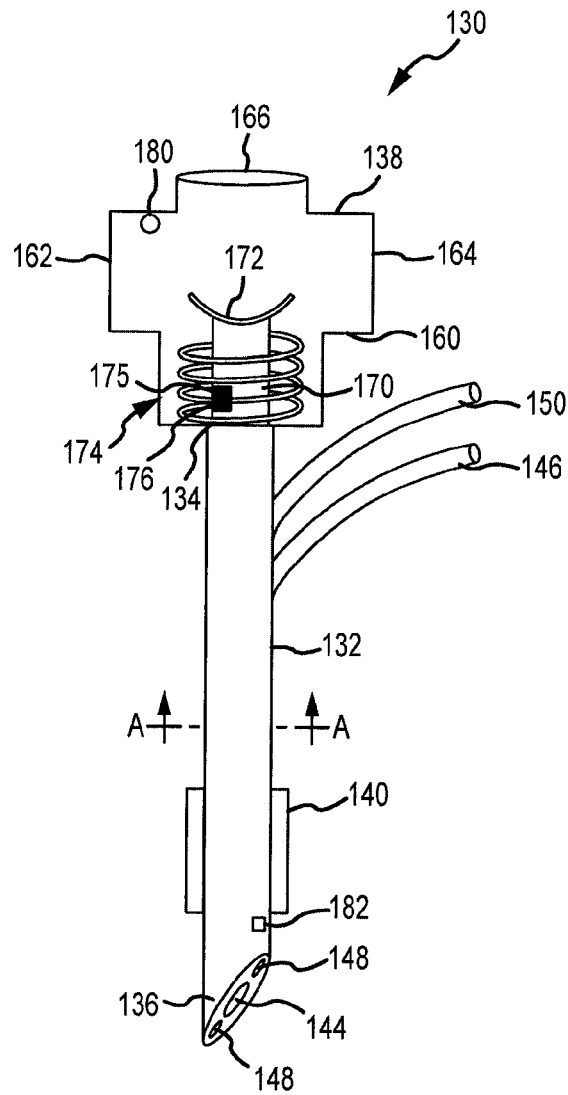
FIG. 7 is a schematic diagram of one system that may be used to enhance circulation while providing adequate oxygen.

Referring to FIG. 7, one embodiment of a system 130 that may be used to enhance circulation while providing oxygen to a patient's lungs will be described. System 130 includes a ventilation tube 132 that is configured to fit within the patient's trachea. Tube 132 has a proximal end 134 and a distal end 136 that may conveniently be tapered to facilitate its introduction. Proximal end 134 may be configured to be permanently or removably attached to a valve system 138. Near distal end 136 is a balloon 140 which may be inflated to secure tube 132 within the trachea and to provide a good seal.

Figure 7A:
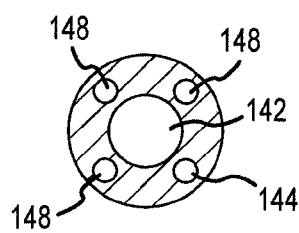
FIG. 7A is a cross sectional view of a ventilation tube of FIG. 7 taken along lines A-A.

As best shown in FIG. 7A, tube 132 includes a central outflow lumen 142 which is used to permit gases to be removed from the patient's lungs and to permit gases to enter (and be forced into) the lungs as described hereinafter. Extending through the outer wall of tube 132 are a variety of other lumens. For example, a lumen 144 may be used to inflate balloon 140. Lumen 144 may extend to a balloon cuff port 146 to permit balloon 140 to be inflated and deflated. The other lumens 148 may be inflow lumens that communicate with an oxygen port 150. In turn, port 150 may be connected to an oxygen source to permit a constant supply of oxygen to be supplied to the lungs.

Valve system 138 comprises a housing 160 that is coupled to ventilation tube 132. Valve system 138 is shown schematically, and it will be appreciated that a variety of valve system could be used, including those described in U.S. Pat. Nos. 6,526,973 and 6,776,156, incorporated by reference. Briefly, valve system 138 comprises inhalation/exhalation ports 162 and 164 that permit air to enter and exit housing 160. Optionally, a port 166 may be provided to permit housing 160 to be coupled to a respiratory bag similar to other embodiments described herein.

Housing 160 is also configured to define an airway 170 that connects to lumen 142 of tube 132. Disposed across airway 170 is a diaphragm 172 that closes whenever there is a vacuum or negative pressure in lumen 144. In this way, respiratory gases are prevented from passing through lumen 144 to the lungs. Such is the case when the patient's chest is expanded or lifted, thereby increasing the negative intrathoracic pressure and enhancing blood circulation. If the patient exhales or the chest is compressed, diaphragm 172 lifts and gases exit lumen 144 through ports 162 and/or 164.

Valve system 130 further includes a threshold valve 174 that comprises an opening 175 airway 170 and flexible member 176. When the negative intrathoracic pressure reaches a threshold amount, member 176 flexes and air enters opening 175 as depicted in FIGS. 8 and 8A. In turn, the air rushes down airway 170 and lumen 144 where it enters the lungs. The threshold actuating pressure may be in the range from about −1 cm $H_2O$ to about −20 cm $H_2O$. Housing 160 may also include a safety threshold valve that could be manually opened or have a low cracking pressure. The safety threshold valve enables a patient to breath through the valve system after restoration of a stable heart rhythm and blood pressure in the event that the rescuer forgets to remove the valve system 138. It may also help to enhance circulation of blood back to the heart and a spontaneously breathing patient, assuming the patient is strong enough to inspire repetitively through about −5 to −7 cm $H_2O$, the cracking pressure of the impedance threshold device. Optionally, a timing light 180 (that may optionally be coupled to a controller) may be used to time chest compressions. Also, an end tidal $CO_2$ sensor 182 may be used to measure $CO_2$ levels.

In use, once tube is secured in the trachea, balloon 140 is inflated. Also, a continuous supply of oxygen is supplied to the lungs through lumens 148. The patient's chest is then compressed and decompressed in an alternating manner. When compressed, air escapes through lumen 144 and lifts diaphragm 172. When decompressed, diaphragm 172 closes airway 170. In so doing, the negative intrathoracic pressure increases until valve 174 opens. Even though oxygen is being supplied through lumens 148, a significant negative pressure is still achieved. Also, since oxygen is being supplied, chest compressions/decompressions may continue without stopping to ventilate. If ventilations are needed, a bag coupled to port 166 may be squeezed.

The invention has now been described in detail for purposes of clarity and understanding. However, it will be appreciated that certain changes and modifications may be practiced within the scope of the appended claims.

What is claimed is:

1. A method for increasing circulation and providing oxygen to a patient in cardiac arrest, said method comprising:
providing an airway having an interface at one end, a valve system at an opposing end and an oxygen lumen, wherein the valve system is configured to prevent air from passing through the airway and to the patient's lungs until a threshold actuating pressure is achieved, and wherein the oxygen lumen passes through the interface and is adapted to transport a continuous supply of oxygen to the patient's lungs, wherein the oxygen lumen is configured to provide the continuous supply of oxygen to the lungs without interfering with operation of the valve system;

coupling the interface to the patient's airway, the interface providing access to the patient's respiratory system;

delivering oxygen through the oxygen lumen and the interface at a rate of between about 1.0 to about 10.0 L/min to provide a continuous supply of oxygen to the patient;

while supplying the oxygen, manipulating a body structure of the patient to increase the magnitude and duration of the patient's positive and negative intrathoracic pressure, wherein during said manipulation the valve system prevents additional respiratory gases from entering the lungs until a negative intrathoracic pressure level in the range from about −1 cm H2O to about −15 cm H2O, the valve system assisting in increasing the magnitude and duration of negative intrathoracic pressure thereby enhancing the amount of blood flow in the heart and lungs and lowering intracranial pressure, therein further increasing blood flow to the brain.

2. A method as in claim 1, wherein the interface comprises a ventilation tube comprising at least an inflow lumen and an outflow lumen, wherein gases exit the patient's lungs through the outflow lumen, and wherein the oxygen is supplied through the inflow lumen.

3. A method in claim 1, wherein the patient is receiving cardiopulmonary resuscitation.

4. A method as in claim 1, wherein the body structure is manipulated by actively compressing the chest and then actively decompressing the chest.

5. A method as in claim 4, wherein the body structure is manipulated using an active compression/decompression device secured to the patient's chest or a vest/carrass that actively expands the chest.

6. A method as in claim 1, further comprising periodically providing a positive pressure breath to the patient.

7. A method as in claim 6, further comprising actively removing carbon dioxide from the patient's lungs.

8. A method as in claim 1, further comprising periodically squeezing the patient's lower limbs.

9. A method in claim 8 wherein the timing of the lower limb compression is synchronized with a decompression phase of CPR.

10. A method for increasing circulation and providing oxygen to a patient, said method comprising:

placing a ventilation tube within the patient's airway, wherein the ventilation tube includes an interface portion for interfacing with the patient, an inflow lumen for permitting oxygen to be supplied to the lungs and an outflow/ventilation lumen separate from the inflow lumen for permitting respiratory gases to be supplied to the lungs and to exit the lungs, wherein a valve system is coupled to the ventilation tube, wherein the valve system is configured to prevent air from passing through the outflow/ventilation lumen and to the patient's lungs until a threshold actuating pressure is achieved, wherein the outflow/ventilation lumen is further configured such that gases exiting the patient may pass through the outflow/ventilation lumen and exit the valve system, and wherein the oxygen lumen passes through the interface portion and is adapted to transport a continuous supply of oxygen to the patient's lungs, wherein the oxygen lumen is configured to provide the continuous supply of oxygen to the lungs without interfering with operation of the valve system;

delivering oxygen through the inflow lumen at a rate of between about 1.0 to about 10.0 L/min to permit a continuous supply of oxygen to be supplied to the patient's lungs;

while delivering oxygen through the inflow lumen, manipulating a body structure of the patient to increase the magnitude and duration of the patient's negative intrathoracic pressure, where in during said manipulation the valve system prevents respiratory gases from entering the lungs through the outflow/ventilation lumen in the ventilation tube until a negative intrathoracic pressure level in the range from about −1 cm H2O to about −15 cm H2O, the valve system assisting in increasing the magnitude and duration of negative intrathoracic pressure thereby enhancing the amount of blood flow in the heart and lungs and lowering intracranial pressure, therein further increasing blood flow to the brain.

11. A method as in claim 10, wherein the body structure is manipulated by actively compressing the chest and allowing the chest to then recoil passively and/or actively, and wherein the patient is in a condition selected from a group consisting of cardiac arrest and hypotension.

12. A method as in claim 10, wherein the valve system includes a threshold inflow valve, and wherein the inflow valve is configured to open if the threshold negative intrathoracic pressure is exceeded.

13. A method as in claim 10, further comprising periodically providing a positive pressure breath to the patient.

14. A method as in claim 13, further comprising monitoring at least one physiological parameter of the person and supplying the positive pressure breath based on the monitored parameter.

15. A method as in claim 14, wherein the physiological parameter comprises end tidal $CO_2$.

16. A method as in claim 10, further comprising interfacing an oxygen source to the inflow lumen to continuously supply the oxygen to the patient's lungs.

17. A method as in claim 10, wherein a balloon is coupled to the ventilation tube, wherein the ventilation tube includes a balloon inflation lumen and further comprising inflating the balloon when within the patient's airway.

18. A system for increasing circulation and providing oxygen to a patient, the system comprising:

an airway;

an interface coupled to one end of the airway that is configured to interface with a patient's airway;

a valve system at an opposing end of the airway, the valve system having an inflow valve that is configured to prevent respiratory gases from flowing to the lungs through the airway until a negative intrathoracic pressure level in the range from about −1 cm H2O to −15 cm H2O;

an oxygen lumen that passes through the interface and is adapted to transport a continuous supply of oxygen to the patient's lungs, wherein the oxygen lumen is configured to provide the continuous supply of oxygen to the lungs without interfering with operation of the valve system;

an oxygen source that is configured to be coupled to the oxygen lumen so as to continuously deliver oxygen through the oxygen lumen at a rate of between about 1.0 to about 10.0 L/min.

19. A device as in claim 18, wherein the airway comprises a ventilation tube that is configured to be placed within the patient's airway.

20. A device as in claim 18, further comprising a manipulation apparatus that is configured to manipulate a body structure of the patient to increase the magnitude and duration of the patient's negative intrathoracic pressure.

21. A device as in claim 18, further comprising at least one physiological sensor to measure at least one physiological parameter of the person.

22. A device as in claim 21, wherein the physiological sensor comprises an end tidal $CO_2$ sensor.

23. A system for increasing circulation and providing oxygen to a patient, the system comprising:
- a ventilation tube that is configured to be placed within the patient's airway, wherein the ventilation tube has a proximal end, a distal end, an inflow lumen to permit oxygen to be supplied to the lungs and an outflow/ventilation lumen to permit respiratory gases to enter the lungs and to exit the lungs;
- a valve system that is configured to be coupled to the outflow/ventilation lumen of the ventilation tube such that gases exiting the patient may pass through the outflow/ventilation lumen and exit the valve system, wherein the valve system includes an inflow valve that prevents respiratory gases from entering the lungs through the outflow/ventilation lumen in the ventilation tube until a negative intrathoracic pressure level in the range from about −1 cm H2O to −15 cm H2O, the inflow valve assisting in increasing the magnitude and duration of negative intrathoracic pressure thereby enhancing the amount of blood flow in the heart and lungs and lowering intracranial pressure, therein further increasing blood flow to the brain;
- an oxygen source that is configured to be coupled to the inflow lumen so as to continuously deliver oxygen through the inflow lumen at a rate of between about 1.0 to about 10.0 L/min without interfering with operation of the valve system.

24. A system as in claim 23, further comprising a manipulation apparatus that is configured to manipulate a body structure of the patient to increase the magnitude and duration of the patient's negative intrathoracic pressure.

25. A system as in claim 24, wherein the manipulation apparatus is selected from a group of apparatus consisting of an active compression/decompression device that is configured to be secured to the patient's chest and a vest/carrass that is configured to actively expand the chest.

26. A system as in claim 23, further comprising a balloon that is coupled to the ventilation tube near the distal end, wherein the ventilation tube includes a balloon inflation lumen.

27. A system as in claim 23, further comprising a device to provide positive pressure ventilation to the patient through the valve system.

* * * * *